United States Patent [19]
Meserol

[11] Patent Number: 5,489,279
[45] Date of Patent: Feb. 6, 1996

[54] METHOD OF APPLYING PHOTODYNAMIC THERAPY TO DERMAL LESION

[75] Inventor: Peter M. Meserol, Montville, N.J.

[73] Assignee: DUSA Pharmaceuticals, Inc., Toronto, Canada

[21] Appl. No.: 215,274

[22] Filed: Mar. 12, 1994

[51] Int. Cl.$^6$ .................... A61M 35/00; A61N 5/06
[52] U.S. Cl. .................. 604/290; 604/20; 607/88; 607/89
[58] Field of Search ................ 604/19, 20, 290; 602/48; 607/88–91, 93

[56] References Cited

U.S. PATENT DOCUMENTS

| | | | |
|---|---|---|---|
| 4,181,128 | 1/1980 | Swartz | 604/20 |
| 4,305,390 | 12/1981 | Swartz | 604/20 |
| 4,402,318 | 9/1983 | Swartz | 604/20 |
| 4,407,282 | 10/1983 | Swartz | 604/20 |
| 4,957,481 | 9/1990 | Gatenby | 604/20 |
| 5,066,274 | 11/1991 | Bummer et al. | 604/20 |
| 5,079,262 | 1/1992 | Kennedy et al. | |
| 5,132,101 | 7/1992 | Vogel et al. | 604/20 |
| 5,143,071 | 9/1992 | Keusch et al. | |
| 5,156,601 | 10/1992 | Lorenz et al. | |
| 5,179,120 | 1/1993 | Vogel et al. | 604/20 |
| 5,215,520 | 6/1993 | Shroot et al. | 604/20 |
| 5,298,502 | 3/1994 | Halling et al. | 514/185 |
| 5,330,452 | 7/1994 | Zook | 602/48 |

*Primary Examiner*—C. Fred Rosenbaum
*Assistant Examiner*—Mark Bockelman
*Attorney, Agent, or Firm*—R. Gale Rhodes, Jr.

[57] ABSTRACT

Method of applying photodynamic therapy to dermal lesion located at a dermal treatment site in skin which includes the stratum corneum, including the steps of hydrating the stratum corneum at the dermal treatment site to enhance the chemical and optical transparency of the stratum corneum at the dermal treatment site and to enhance the passage therethrough of photopharmaceutical and light, introducing photopharmaceutical into the treatment site through the hydrated stratum corneum, and introducing light into the treatment site through the hydrated stratum corneum to photoactivate the photopharmaceutical to treat the dermal lesion.

6 Claims, 2 Drawing Sheets

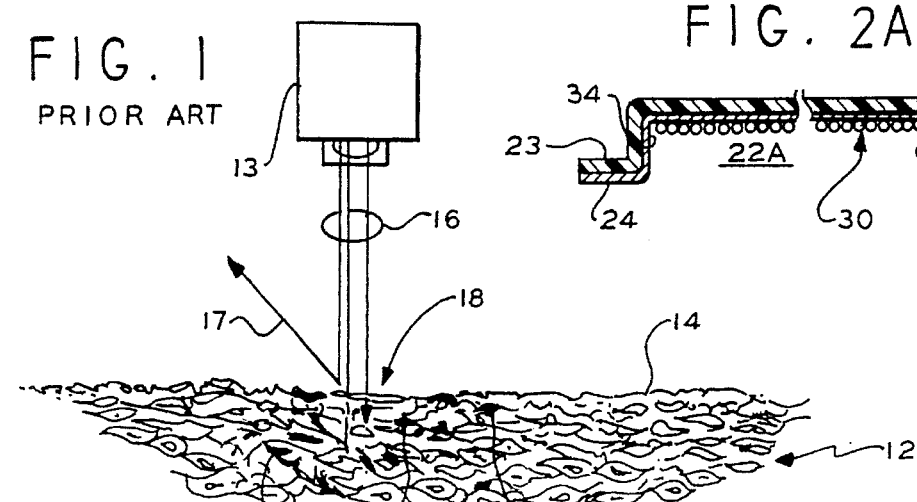
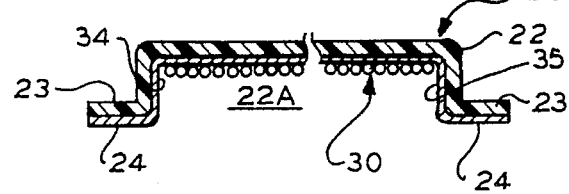
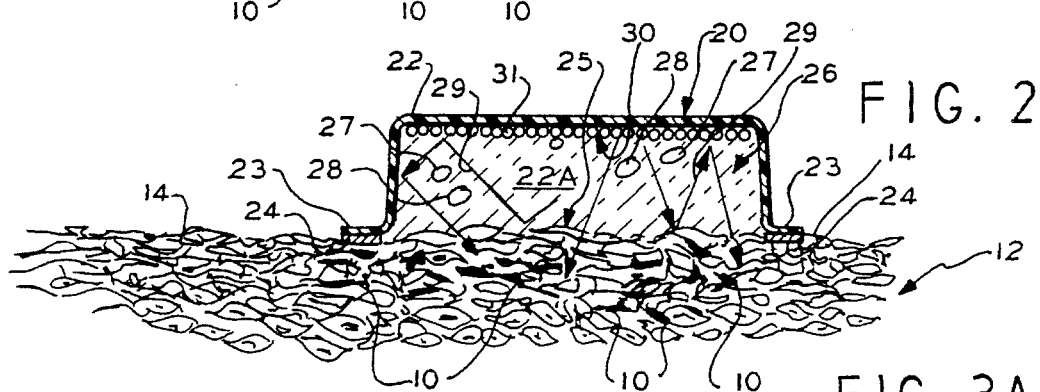
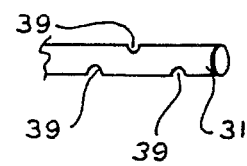
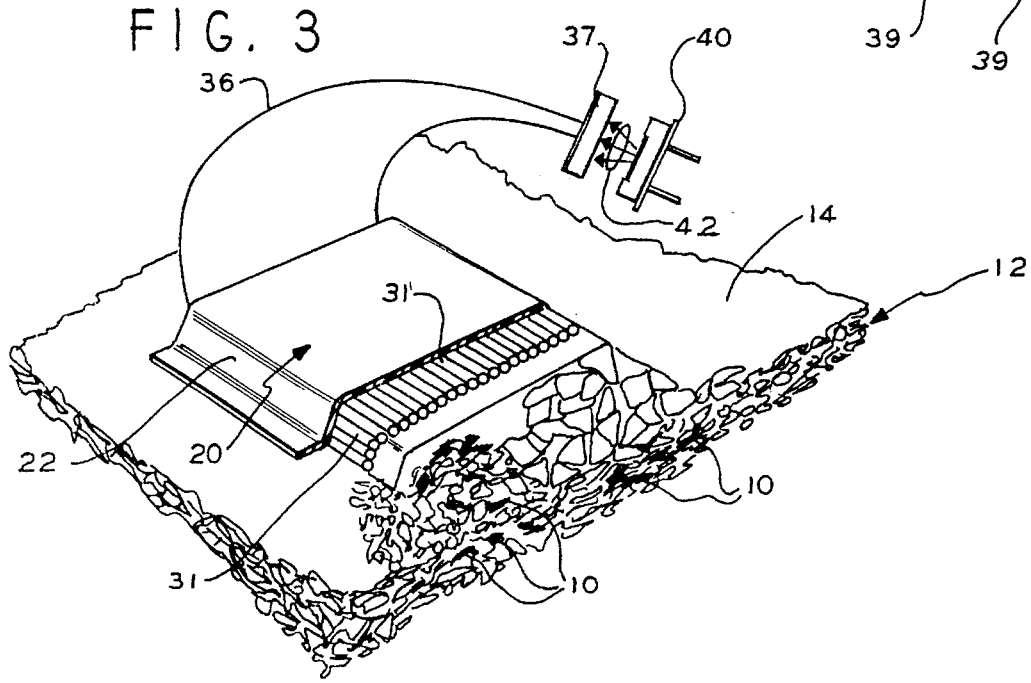

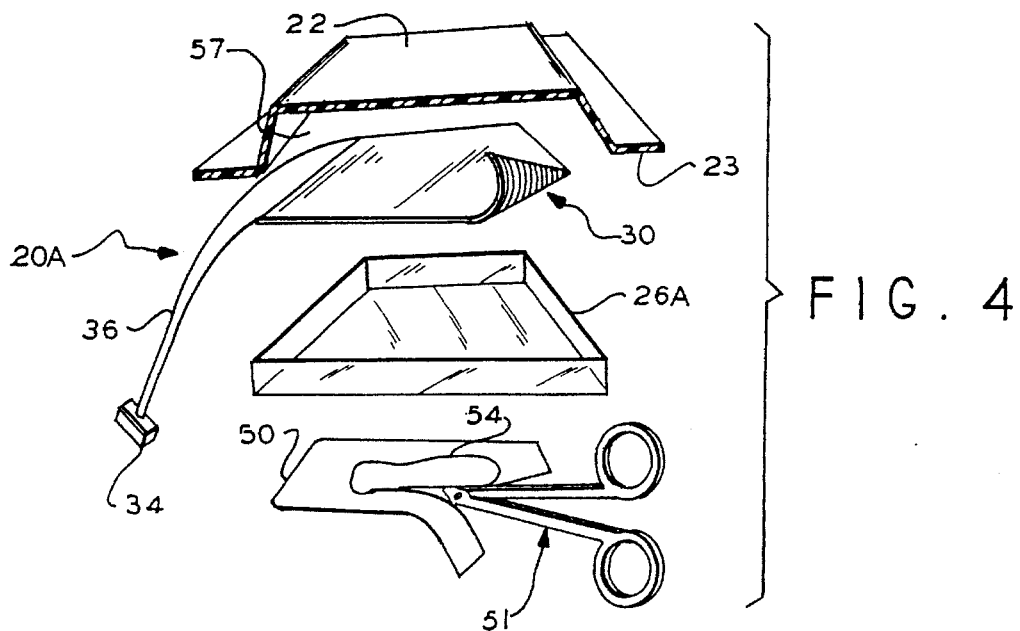
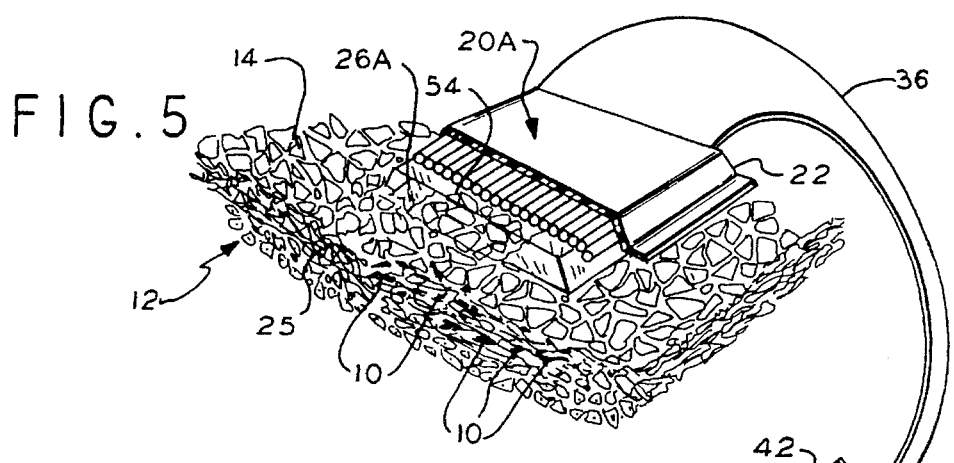
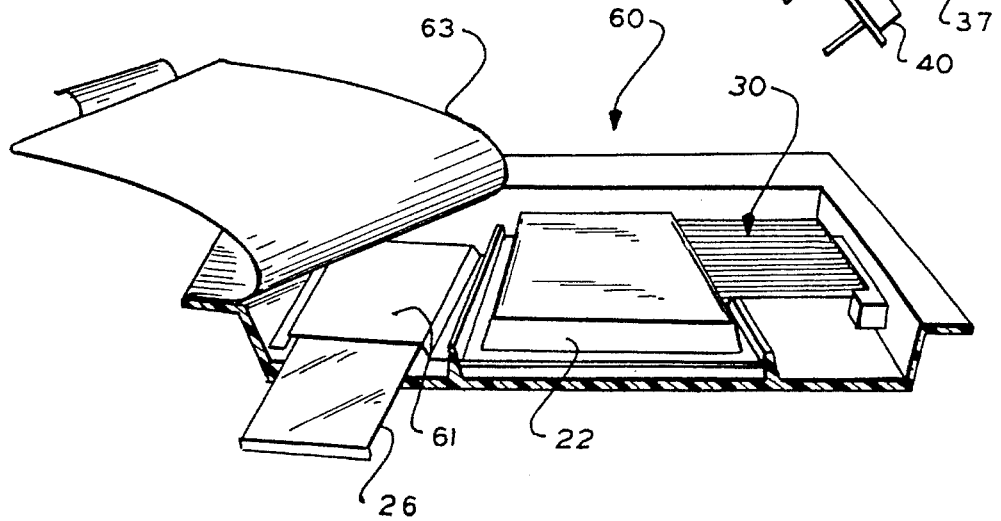

5,489,279

METHOD OF APPLYING PHOTODYNAMIC THERAPY TO DERMAL LESION

BACKGROUND OF THE INVENTION

This invention relates generally to a method of applying photodynamic therapy (PDT) to dermal lesions located at a dermal treatment site in the skin which includes the stratum corneum, such dermal lesions include, for example, actinic keratosis, basal carcinoma and psoriasis. More particularly, this invention relates to a method of applying photodynamic therapy to a dermal lesion including the steps of hydrating the stratum corneum to enhance its optical and chemical transparency or transmissiveness and introducing photopharmaceutical and light through the hydrated stratum corneum to photoactivate the photopharmaceutical and cause it to biologically engage and treat the dermal lesion. In a preferred embodiment, the method of the present invention utilizes a hydrogel containing hydration agent and photopharmaceutical to fluidically couple the photopharmaceutical to the hydrated stratum corneum and to optically couple the light to the hydrated stratum corneum to photoactive the photopharmaceutical through the hydrated corneum to cause the photoactivated photopharmaceutical to biologically engage and treat the dermal lesions.

Bodies, sheet or layer forms, of transparent (to light) hydrogel or hydrogel materials are well known in the medical field and may comprise, for example, a polyvinyl alcohol with a water matrix; some of these transparent hydrogels are castable into intimate physical and optical contact with other devices. They have been widely adapted to such applications as diagnostic electrodes (for EKG), wound care dressings, and transdermal delivery devices for systemic delivery of pharmaceutical agents. The biocompatability of this class of materials is well established for extended contact with dermal structures. Much of the prior art in medical applications for hydrogel or hydrogel materials teaches devices and methods for electrical conductivity enhancement. Critical in using hydrogel in many medical applications, such as an electrical interface, is the ability of the hydrogel to form intimate physical contact with skin or dermal structures. U.S. Pat. No. 5,143,071 issued to Keusch et al. on Sep. 1, 1992, cites an extensive list and description of prior art hydrogels suitable for this purpose, and this patent is incorporated herein by reference.

A concurrent body of prior art embraces hydrogels or hydrocolloids, as wound dressings and dressings impregnated with pharmaceutical compounds; representative of this prior art is U.S. Pat. No. 5,156,601 to Lorenze et al. Further, the work of Gombotz et al., Proc. Intl. Symp. Cont. Rel. Bioact. Mtl., Vol. 19, 1992, describes the rapid release of complex compounds from hydrogels to skin or dermal structures.

U.S. Pat. No. 5,079,262 issued to Kennedy et al. discloses a method of detection and treatment of malignant and non-malignant lesions utilizing 5-aminolevulinic acid. The acid is administered to a patient in an amount sufficient to induce synthesis of protoporphyrin IX in the lesions, followed by exposure of the treated lesions to a photoactivating light in the range 350–640 nm. The acid is administered to the patient orally, topically or by injection, but not through a hydrogel coupling; this patent is incorporated herein by reference.

None of the prior art references teach or suggest a method for applying photodynamic therapy to dermal lesions using transparent hydrogel as a coupling agent to skin for light and photopharmaceutical. Since its first reported clinical use at the turn of the century, photodynamic therapy has been accomplished using light projected to the dermal treatment site from sources at some distance from the site. Modern photodynamic therapy (from 1978 onwards) has developed light delivery protocols using artificial sources such as tungsten halogen, or xenon arc lamps with wavelength filtration to activate photopharmaceuticals. All of the above light sources have been used in projective, field illuminating devices that flood the target treatment field or site in the treatment of superficial cutaneous lesions with light containing a wavelength designed to activate the photopharmaceutical.

In the case of the tungsten and xenon-arc sources, extensive filtration of the available light flux is essential to restrict the delivered energy to appropriate wavelengths that photoactivate the photopharmaceutical in the target dermal structures. Colored glass or interference filters used with these sources transmit some portion of unwanted wavelengths, notably in the infrared region, and can cause thermal effects that may mask the effect of photoactivity with an undesirable heating effect that also preferentially damages malignant tissue. High-power surgical lasers, even when de-focussed, also can induce undesirable thermal effects. The work of Svaasland, Photochem/Photobiol. 1985, measured this effect and its impact on PDT protocols.

Dosmetry of delivered photodynamically effective light to a dermal treatment site is extremely difficult using current projective optics. Mathematical modeling of skin optics has been a slow and difficult process. Recent publications by Van Gemert et al., IEEE Trans. Biomed. Eng., Vol. 36;12, 1989, critically reviewed the prior work and presents a 4-layer model of light-dermal tissue interaction; this publication is incorporated herein by reference. Van Gemert et al. elaborates on the advantages and effectiveness of the diffusion model of light transport in tissue, which depends upon the efficient coupling of the externally applied light to the target tissue. A later publication by R. Rox Anderson, Optics of the Skin, Clinical Photomedicine, Dekker Publication, 1993, reviews the two basic processes which govern the optics or behavior of light in skin, namely, light absorption and light scattering; this publication is incorporated herein by reference.

It has been found that an efficient and practical method of establishing the diffusion conditions of light transport is to provide a transparent coupling means that is in intimate contact with the dermal lesions on one surface and with the light source on its opposite surface. Under these conditions reflective losses are reduced, and delivered energy is much more efficiently transmitted into the target region.

The stratum corneum present at a dermal treatment site on the skin of a person is a formidable barrier to transport (transmission, penetrability or permeability) of light into the deeper structures of the skin where dermal lesions typically reside, in whole or in part. The layered plate-light corneocytes comprising the stratum corneum constitute an efficient reflective optical surface which reflects nearly all light in the visible spectrum. There is some transmission in the region of 590 to 700 nanometers. Photopharmaceuticals are formulated to be activated by light energy in this region. Penetration depth is in the region of 1–3 mm from the dry corneocyte surface. It has been discovered that the interposition of a flexible transparent hydrogel coupling layer between a monochromatic plate or sheet-formed light source and the skin surface constitutes a new and more efficient delivery method of activating optical energy to target dermal lesions for photodynamic therapy; particularly where the monochromatic light source delivers light at the specific wavelength at which the photopharmaceutical is photoactivated.

There are other substantial benefits that attend to a method of applying PDT using an intimately contactive hydrogel coupling layer. Because hydrogels are typically 60 to 90% water, hydration of the stratum corneum occurs rapidly following the method step of contacting the stratum corneum with the hydrogel sheet. This hydration has a substantial optical transparency, or optical transmissiveness, enhancing effect, allowing more light to pass through the hydrated stratum corneum. Although the mechanism of this optical transparency has not been extensively studied, it is thought to result from a reduction of the light reflectivity of the stratum corneum through softening of the corneocytes by a solvent or plasticizing action.

It is well established in the literature of chemical transport through the skin that hydration can enhance the chemical transparency, transmissiveness, permeability, passage or transport of pharmaceuticals through the stratum corneum. A review and discussion of this enhanced transport under hydrated conditions is found in Ghosh et al., Pharmaceutical Tech., April 1993, which publication is incorporated herein by reference.

It follows that there are two key method steps of applying PDT to dermal structures where the protocol requires topical application of the photopharmaceutical. The step of transporting the photopharmaceutical into target tissue, and the subsequent step of light activating of the photopharmaceutical at the target tissue, these steps can be more efficiently accomplished using the diffusion route for both the drug and the activation optical energy.

It has been found that using transparent hydrogel as a coupling layer in the method of the present invention serves the dual purpose of establishing conditions for the optical energy diffusion into skin tissue and photopharmaceutical compound diffusion or other introduction into skin tissue, by the intercellular or transcellular routes; however, it will be understood that the introduction of the photopharmaceutical from the hydrogel into the hydrated skin or through the hydrated stratum corneum, depending on the specific photopharmaceutical used, can be by the above-noted diffusion, or by absorption, or by other mechanism constituting chemical permeation or penetration of the hydrated skin or stratum corneum. A third optical advantage of a transparent transport hydrogel is that it can remain in place after PDT exposure, as a protective dressing.

It is an object of this invention to provide a method of applying PDT to dermal lesion which combines the delivery of a photopharmaceutical and light for photodynamic therapy of dermal lesions utilizing a transparent carrier, reservoir, or transport, of hydration agent and photopharmaceutical, and which transparent transport acts as an efficient coupler between a light source and the dermal surface.

In the preferred embodiment of this method invention, a transparent hydrogel is used to serve as a transport or reservoir of a hydration agent and photopharmaceutical and which hydrogel rapidly releases the photopharmaceutical to the skin tissue. For purposes of practicing photodynamic therapy, rapid delivery is desirable. This contrasts with prior art transdermal methods and devices for non-PDT drug delivery which seek to provide much slower release kinetics for system absorption. Further, in the method of the present invention, the photodynamic therapy is applied locally to a dermal treatment site defined by a cover, container or patch covering the dermal treatment site where the dermal lesion is located and delivering the light necessary to activate the photopharmaceutical only to the dermal treatment site. It is thus advantageous to rapidly deliver the light activated photopharmaceutical doses to skin tissue, and dermal lesion, and then deliver the light dose to initiate its biological activity to treat the dermal lesion.

The intimate transparent hydrogel contact established at the skin surface of the treatment site in the present method invention forms both a fluid or fluidic coupling for the photopharmaceutical and an optical or optic coupling for the photoactivating light. In the case of the fluidic coupling, the water contained in the hydrogel matrix begins to solubilize the stratum corneum, hydrating this normally dry layer, and forms an avenue of exchange between the hydrogel and the dermal lesion. Hydration enhances both intracellular and transcellular pathways. Upon establishment of these pathways, transport of the photopharmaceutical to target tissue or dermal lesion commences.

The effect of hydration on fluid transport across the stratum corneum layer is substantial. Normally this structure contains 10–15% water. Hydrated stratum corneum can retain up to 50% water and the normal light diffusion coefficient of the hydrated stratum corneum can increase ten-fold.

The effect of hydration on optical coupling of light into skin tissue is also substantial, but is sustainable only with the contact of the transparent hydrogel to both the skin tissue and the light source. In an example of an embodiment of the method of the present invention a fiber optic panel comprising a plurality of fiber optic strands is used for delivering light to activate the photopharmaceutical, and hydrogel contact with the fiber optic strands is efficient because at manufacture the hydrogel is cast against the fiber optic strands and conforms to the regular geometry of these strands. The formation of the hydrogel to skin surface juncture occurs at the point of engagement of the hydrogel to the skin surface. The physical characteristics of the hydrogel necessary to establish intimate skin contact are those described for electrode contact in the prior art references, cited above. Similar characteristics are required for applying PDT with the present invention, with the added hydrogel attributes of light transmission and hydration of the skin.

The mechanical changes hydration produces in the stratum corneum layer have substantial impact on the optical coupling efficiency of externally applied light in the red region of the spectrum. The ultra-structure of the stratum corneum is an array of flattened essentially dead cells which are constantly being shed in a natural process of skin surface renewal. This results in a very uneven, dry, and highly light reflective layer or barrier to light penetration or transmission. Hydration by contact with emollients and oil-based unguents confers an improved surface but the effect is transitory under projected optical illumination schemes that, through surface heating, rapidly degrade the hydration effect by drying out of the target region. Thus though topically applied agents for PDT may briefly induce an optical improvement, it rarely persists through the projected light illumination phase if surface heating occurs during illumination.

This is in marked contrast with the present invention, where the hydrogel remains in place during the light dosage and serves as a hydration agent and photopharmaceutical reservoir or transport means, and conduit and coupling for both light and fluidized agents to the target tissue or dermal treatment site during all phases of photodynamic therapy of a dermal lesion.

SUMMARY OF THE INVENTION

Method of applying photodynamic therapy to dermal lesion located at a dermal treatment site in skin which includes the stratum corneum, including the steps of hydrating the stratum corneum at the dermal treatment site to enhance the chemical and optical transparency of the stratum corneum at the dermal treatment site and to enhance the passage therethrough of photopharmaceutical and light, introducing photopharmaceutical into the treatment site through the hydrated stratum corneum, and introducing light into the treatment site through the hydrated stratum corneum to photoactivate the photopharmaceutical to treat the dermal lesion.

DESCRIPTION OF THE DRAWINGS

FIG. 1 is a diagrammatical illustration, substantially in cross-section, illustrating prior art photodynamic therapy of a dermal lesion using projection optics;

FIG. 2 is a diagrammatical illustration, substantially in cross-section, illustrating a first embodiment of a device or apparatus for practicing the method of the present invention;

FIG. 2A is a partial cross-sectional view of the cover of the device shown in FIG. 1 and which illustrates that the internal surface of the cover may be provided with a suitable light reflecting layer or coating;

FIG. 3 is a perspective cut away diagrammatical illustration of the device of FIG. 2 shown in situ over a dermal treatment site for practicing the method of the present invention;

FIG. 3A is a partial perspective view of an optical fiber strand illustrating diagrammatically the lateral or radial exiting of laser light;

FIG. 4 is an exploded view, partially in cross-section, illustrating a second device or apparatus for practicing the second embodiment of the method of the present invention;

FIG. 5 is a perspective diagrammatical illustration, substantially in cross-section, illustrating the practice of the second embodiment of the method of the present invention with the device or apparatus for practicing the method shown in situ over a dermal treatment site; this FIG. also shows the connection to a laser diode, and in cross-section, illustrates a procedure tray containing the components of the device apparatus for practicing the first embodiment of the method present invention; and FIG. 6 is a perspective view of a procedure tray of the present invention.

DETAILED DESCRIPTION OF THE PREFERRED EMBODIMENTS

FIG. 1 illustrates prior art photodynamic therapy of dermal lesions 10 located in a person's skin indicated by general numerical designation 12, which skin includes the stratum corneum 14. [It will be understood that the dermal lesions 10 are illustrated diagrammatically in FIG. 1, and in FIGS. 2, 3 and 5 referred to below, by the darkest spots shown in the skin 12. It will be further generally understood that the dermal lesions 10 are generally located under the stratum corneum 14 or within the skin 12 or can extend partly outwardly of the skin as illustrated in FIG. 1.] Projective light source 13 directs light, indicated by arrows 16, onto the skin 12 and, as noted generally above, the stratum corneum 14 scatters the light with substantial portions of the light, as indicated by arrow 17, being reflected away from the stratum corneum 14 and thereby not initiating any photodynamic therapy. However, as further noted above, red light within the light 16 can penetrate the skin 12 to 3–4 mm. The projective light source 13 is typically either a filtered incandescent source or a laser and is normally arranged to project the light 16 perpendicular to the skin 12 and corneum 14. It will be further understood from FIG. 1 that the dermal treatment site, indicated generally by numerical designation 18, is generally not well defined in distinction to the dermal treatment site produced by the present invention described below and illustrated particularly in FIG. 2.

Referring to FIG. 2, a device or apparatus for practicing the first embodiment of the method of the present invention is indicated by general numerical designation 20. Device 20 includes a cover 22, which may be also referred to as a container or patch, and may be made, for example, of Mylar and suitably formed into the shape shown such as for example by vacuum forming. It will be noted that the lower portion of the cover 22 may be provided with an outwardly extending flange or peripheral portion 23 circumscribing the lower cover portion, and which peripheral portion 23 may be provided with a suitable layer of adhesive 24, of the type known to the art to be compatible with the human skin, for sealingly engaging the skin 12 to seal the cover 22 to the skin and define and cover a dermal treatment site indicated by general numerical designation 25; the flange or peripheral portion 23 and adhesive layer 24 are better seen in FIG. 2A. It will be noted that in the present invention, FIG. 2, the dermal treatment site 25 is comparatively narrowly and well defined as contrasted to the open and comparatively poorly defined prior art dermal treatment site 18 illustrated in FIG. 1. The cover 22 provides an internal chamber 22A, better seen in FIG. 2A, opposite the dermal treatment site 25 and a body or layer of transparent hydrogel 26 is received and resides within the chamber 25. Transparent hydrogel 26 may be a transparent hydrogel of the type described above and may be, for example, a polyvinyl alcohol having a water matrix which water serves as a hydration agent in the present invention; the water or hydration agent is illustrated diagrammatically in FIG. 2 by circles 27. In addition to containing the water or hydration agent 27, the transparent hydrogel 26 includes a suitable photopharmaceutical for treating the dermal lesion 10 and which photopharmaceutical is illustrated diagrammatically in FIG. 2 by the circles 28; the photopharmaceutical 28 may be introduced into the transparent hydrogel 26 by absorption. The photopharmaceutical 28 may be, for example, photopharmaceutical 5-ALA available from the Sigma Chemical Company, St. Louis, Mo., and which photopharmaceutical is made photoactive by red light at a wavelength of substantially 635 nm.

The device 20, FIG. 2, further includes a light delivery source indicated by general numerical designation 30 and which may be an optic laser light-emitting panel available from Lasermax, Inc., of Rochester, N.Y. which emits monochromatic red light having a wavelength of substantially 635 nm so as to be photoactively compatible with and matched to the photoactive wavelength of the photopharmaceutical 28 contained in the transparent hydrogel 26. The optic laser light-emitting panel 30 includes a plurality of optical fiber strands 31 indicated in transverse cross-section by the linearly aligned circles shown in FIG. 2 and which strands 31 may be better seen in cylindrical perspective view in FIG. 3. Referring to FIG. 2A, the cover 22 includes an internal surface 34 which may be provided with a suitable layer or coating of reflective material 35 which may be a layer of suitable reflective foil suitably adhesed to the internal surface 34, or thermally staked thereto, or may be a suitable reflective coating provided by a suitable deposition process; reflective layer 35 is not shown in FIG. 2 since it is relatively thin as compared to the cover 22 but it will be understood that such reflective layer is present in device 20 of FIG. 2. The optic laser light-emitting panel 30 resides within the chamber 25 and may be suitably secured to the cover 22, and to or through the reflective layer 35, by a suitable adhesive or by suitable thermal staking. The transparent hydrogel 26 is castable transparent hydrogel and is cast into intimate physical and optical contact with the optical fiber strands 31.

Referring to FIG. 3, it will be understood that the strands of optical fibers 31 of the optic laser light-emitting panel 30 are actually the ends or end portions of the optical fibers contained in the optical fiber bundle 36 which terminate in a suitable optical fiber connector 37; as shown in FIG. 4, the cover 22 is provided with a suitably sized opening 57 for admitting the fiber bundle therethrough. Connector 37 is for being connected to a suitable laser diode 40 for producing, in the preferred embodiment, monochromatic red light indicated by the arrows 42 having a wavelength of substantially 635 nm; the laser diode 36 may be, for example, a told 635 available from Toshiba Optical Systems. The laser light 42 is transmitted or ducted to the optical strands 31, through the optical bundle 36 and, as may be understood from FIG. 3A, the optical fiber strands 31 are provided with side openings or lateral notches 39 which cause or permit the laser light 42 (FIG. 3) to be emitted at a number of angles from the sides of the strands 31 but which light is ultimately reflected by the reflective layer or surface 35 (FIG. 2A) and caused to ultimately impinge upon the stratum corneum 15 and skin 12. As may be noted in FIG. 2, the laser light, as indicated by the arrows 29, is reflected off the reflective surface 35 (FIG. 2A) and transmitted through the transparent hydrogel 26.

Upon the device 20, FIGS. 2 and 3, being sealingly engaged to the skin 12 and stratum corneum 14 as illustrated in FIGS. 2 and 3 and described above, the first embodiment of the method of the present invention is practiced. Water or hydration agent 27 contained in the transparent hydrogel 26 engages the stratum corneum 14 and immediately begins to hydrate and soften the stratum corneum to enhance its optical transparency or transmissiveness to facilitate the transmission of the laser light 37 therethrough and to enhance its chemical transparency or transmissiveness to facilitate the transmission therethrough of the photopharmaceutical 28 and into the dermal treatment site 25 containing the dermal lesion 10. The laser light 42 (FIG. 3) is introduced into the dermal treatment site 25 and illuminates the site by light diffusion which photoactivates the photopharmaceutical 28 to initiate its biological activity and to cause the photoactivated photopharmaceutical to biologically engage and treat the dermal lesion 10. After such treatment, as noted generally above, the cover 22 of the device 20 may remain in place after the photodynamic therapy as a temporary protective dressing for the dermal treatment site 25. It will be further understood that a biologically sufficient quantity of photopharmaceutical is introduced into the hydrogel to accomplish treatment of the dermal lesion.

Referring now to FIGS. 4 and 5, a device or apparatus for practicing a second embodiment of the method of the present invention is shown and indicated by general numerical designation 20A. The structural elements in the device 20A which are the same, or substantially the same, as the corresponding structural elements in device 20 of FIGS. 2 and 3, are given the same numerical designation as the elements in FIGS. 2 and 3. It will be generally understood that method practiced by device 20A for applying photodynamic therapy to dermal lesions 10, FIG. 5, in substantially the same as the method practiced by the device 20 of FIGS. 2 and 3. However, in the embodiment 20A, the transparent hydrogel 26A while including the water or hydrating agent indicated by circles 27 in FIG. 2, does not contain the photopharmaceutical indicated by circles 28 in FIG. 2. Device 20A further includes a second layer or sheet of transparent hydrogel 50 which is smaller in size or thickness than transparent hydrogel 26A and which, although containing a water matrix in which the photopharmaceutical is contained, is highly dehydrated as compared to the transparent hydrogel 26A. The relatively highly dehydrated state of the transparent hydrogel 50 permits the transparent hydrogel 50 to be cut and trimmed, such as by a pair of scissors 51, into a body of hydrogel 54 having a size much smaller than the transparent hydrogel 26A and shaped into substantially the same shape as the underlying dermal lesion 10, FIG. 5. As is known, the photopharmaceutical contained in the transparent hydrogel 50 is toxic, typically acidic, and its application to the skin of a patient can be at least somewhat painful. It has been discovered that by reducing the size of the hydrogel containing the photopharmaceutical a reduced but still biologically sufficient quantity of photopharmaceutical can be applied photodynamically to the patient but with reduced discomfort. This also facilitates a photopharmaceutical profile that minimizes the application of the photopharmaceutical to healthy tissue at the dermal treatment site 25, FIG. 5, yet allows the controlled delivery of photoactivating light to the entire dermal treatment site 25. In the practice of the method of application of photodynamic therapy, the trimmed hydrogel 54 resides within the cover 22 intermediate the transparent hydrogel 26A and the treatment site 25 as may be noted particularly from FIG. 5. The transparent hydrogel 26A and trimmed hydrogel body 54 function in substantially the same manner as the single layer of transparent hydrogel 26 in device 20 of FIGS. 2 and 3 to apply photodynamic therapy to the dermal lesion 10.

A procedure tray is indicated by general numerical designation 60. Procedure tray, FIG. 6 60 is a single use procedure tray and may be suitably thermoformed from a suitable plastic such as polypropylene; in the preferred embodiment the devices 20 and 20A are single use devices. The tray is compartmentalized, as shown, to receive, for example, the components or elements comprising the article of manufacture 20 shown in FIGS. 2 and 3. The transparent hydrogel 26 may be received within a moisture impervious foil or laminate pouch 61, the cover 22 and optic laser light emitting panel 30 may be received in compartments as shown also. The procedure tray 60 is sealed against moisture variation by a "peelable" foil sealing panel 63. The sealing panel 28 is removed and the elements or components of the article of manufacture 20 are assembled as illustrated in FIGS. 2 and 3 and thereafter may be applied to the skin as described above and illustrated diagrammatically in FIGS. 2 and 3.

It will be understood that the term photopharmaceutical as used herein and in the appended claims means an agent which is itself a photosensitizer or which is converted to a photosensitizer in the body.

It will be understood that many variations and modifications may be made in the present invention without departing from the spirit and the scope thereof.

What is claimed is:

1. Method of applying photodynamic therapy to dermal lesion located in skin which includes the stratum corneum, comprising the steps of:

defining a dermal treatment site over the dermal lesion to provide a defined dermal treatment site;

hydrating the stratum corneum at said defined dermal treatment site by placing transparent hydrogel containing a hydrating agent and 5-ALA photopharmaceutical into intimate contact with the stratum corneum at said defined dermal treatment site to enhance the chemical and optical transparency of the stratum corneum at said defined dermal treatment site and to enhance the passage therethrough of said photopharmaceutical and light;

utilizing said transparent hydrogel to fluidly couple and introduce said photopharmaceutical into said defined dermal treatment site and through the hydrated stratum corneum at said defined dermal treatment site and to the dermal lesion; and utilizing said transparent hydrogel to optically couple and introduce monochromatic red light at substantially 635 nm into said defined dermal treatment site and through the hydrated stratum corneum at said defined dermal treatment site to photoactivate the photopharmaceutical at the dermal lesion to cause said photoactivated photopharmaceutical to biologically engage and treat the dermal lesion; and leaving said transparent hydrogel in place over said defined dermal treatment site while said light is being introduced therethrough.

2. Method of applying photodynamic therapy to dermal lesion located in skin which includes the stratum corneum, comprising the steps of:

defining a dermal treatment site over the dermal lesion to provide a defined dermal treatment site;

providing a body of transparent flexible hydrogel including 5-ALA photopharmaceutical and a water matrix which water acts as a hydrating agent;

engaging the dermal treatment site with said hydrogel to cause said water to hydrate the stratum corneum at said dermal treatment site to enhance the chemical and optical transparency of the stratum corneum at said dermal treatment site and to cause said 5-ALA photopharmaceutical to be introduced through the hydrated stratum corneum and to the dermal lesion at said defined dermal treatment site; and applying monochromatic red light at substantially 635 nm through said transparent hydrogel at said defined dermal treatment site to photoactivate said photopharmaceutical at said dermal lesion to cause said photoactivated photopharmaceutical to biologically engage and treat the dermal lesion at said defined dermal treatment site.

3. Method of applying photodynamic therapy to dermal lesion located at a dermal treatment site in skin which includes the stratum corneum, comprising the steps of:

providing first and second transparent bodies of hydrogel, said bodies of hydrogel including a water matrix and said water in said first body of hydrogel acting as a hydrating agent, said second body of hydrogel being less hydrated than said first body of hydrogel and being sufficiently dehydrated to permit said second body of hydrogel to be cut, and introducing 5-ALA photopharmaceutical into said second body of hydrogel;

cutting said second body of hydrogel into substantially the same shape as the dermal lesion;

applying said bodies of hydrogel to said dermal treatment site with said second body of hydrogel being in direct engagement with the skin at the dermal treatment site to cause said water in said first body of hydrogel to hydrate the stratum corneum at the dermal treatment site to soften and render the stratum corneum there at more transparent to the passage therethrough of photopharmaceutical and light and to cause said 5-ALA photopharmaceutical to be introduced into the dermal treatment site; and introducing monochromatic red light at substantially 635 nm into the dermal treatment site through the transparent bodies of hydrogel and softened stratum corneum to photoactivate said photopharmaceutical at the dermal treatment site to cause the photoactivated photopharmaceutical to biologically engage and treat the dermal lesion.

4. Method of applying photodynamic therapy to dermal lesion located at a dermal treatment site in skin which includes the stratum corneum, comprising the steps of:

using transparent hydrogel containing 5-ALA photopharmaceutical and water which water acts as a hydrating agent to hydrate the stratum corneum overlying the dermal lesion and using said water to fluidly couple and introduce said photopharmaceutical through the hydrated stratum corneum to the dermal lesion; and using said transparent hydrogel to optically couple the monochromatic light at substantially 635 nm to the hydrated stratum corneum and to introduce the light through the hydrated stratum corneum to photoactivate the photopharmaceutical at the dermal lesion to cause the photoactivated photopharmaceutical to biologically engage and treat the dermal lesion.

5. In the method of treating dermal lesion including the steps of introducing photopharmaceutical to dermal lesion and introducing light to the photopharmaceutical at the dermal lesion to photoactivate the photopharmaceutical to treat the dermal lesion,

WHEREIN THE IMPROVEMENT COMPRISES:

introducing 5-ALA photopharmaceutical into transparent hydrogel including a water matrix which acts as a hydrating agent; and using said hydrogel to couple said photopharmaceutical and light to the stratum corneum of skin substantially overlying the dermal lesion to hydrate the stratum corneum to enhance its transmissiveness to said photopharmaceutical and light and introducing said photopharmaceutical to the dermal lesion through the hydrated stratum corneum and introducing monochromatic red light at substantially 635 nm through the transparent hydrogel and softened stratum corneum to photoactivate said photopharmaceutical and to cause the photoactivated photopharmaceutical to biologically engage and treat the dermal lesion.

6. In the method of treating dermal lesion including the steps of introducing photopharmaceutical to dermal lesion and introducing light to the photopharmaceutical at the dermal lesion to photoactivate the photopharmaceutical to treat the dermal lesion,

WHEREIN THE IMPROVEMENT COMPRISES:

introducing 5-ALA photopharmaceutical into transparent hydrogel comprised of a homogeneous uniform mixture of water and at least one water-soluble high molecular weight polymer which acts as a hydrating agent; and using said hydrogel to couple said photopharmaceutical and said light to the stratum corneum of skin substantially overlaying the dermal lesion to hydrate the stratum corneum sufficiently to enhance its transmissiveness to said photopharmaceutical and said light and introducing photopharmaceutical to the dermal lesion through the hydrated stratum corneum and introducing monochromatic red light at substantially 635 nm through the transparent hydrogel and hydrated stratum corneum to photoactivate said photopharmaceutical and at the dermal lesion to cause the photoactivated photopharmaceutical to biologically engage and treat the dermal lesion.

* * * * *